United States Patent [19]
Slaugh

[11] Patent Number: 4,789,502
[45] Date of Patent: Dec. 6, 1988

[54] CARBOXYLIC ACID PRODUCTION

[75] Inventor: Lynn H. Slaugh, Cypress, Tex.

[73] Assignee: Shell Oil Company, Houston, Tex.

[21] Appl. No.: 934,296

[22] Filed: Nov. 24, 1986

[51] Int. Cl.$^4$ .......................... C11C 1/00; C07C 51/16
[52] U.S. Cl. .................................. 260/413; 260/410.5; 260/410.9 R; 502/73; 502/75; 502/84; 502/87; 502/244; 502/302; 502/307; 502/318; 562/418; 562/538
[58] Field of Search ............... 562/418, 420, 421, 538, 562/540; 260/413; 502/73, 75, 84, 87, 243, 244, 302, 307, 317, 318

[56] References Cited
U.S. PATENT DOCUMENTS
4,220,803 9/1980 Marcinkowsky et al. .......... 562/538

FOREIGN PATENT DOCUMENTS
102835 6/1982 Japan .

OTHER PUBLICATIONS
Goldschmidt et al, "The Formation of Acids from Aldehydes and Steam", Ber., V. 67 (1934), pp. 202–213.

Primary Examiner—Werren B. Lone
Assistant Examiner—Vera C. Clarke

[57] ABSTRACT

Carboxylic acids are produced in high yield by contacting alcohols, water and hydrogen with a Cu-Zn-Cr-base promoter/alumina catalyst.

12 Claims, No Drawings

CARBOXYLIC ACID PRODUCTION

FIELD OF THE INVENTION

This invention relates to an improved process for converting alcohols and water into carboxylic acids by use of a catalyst comprising copper, zinc, chromium, alkali or alkaline earth metal or rare earth metal supported on an alumina support.

BACKGROUND OF THE INVENTION

Carboxylic acids find many uses in industry. The lower molecular weight acids are frequently used as intermediates; such as acetic acid being used in the preparation of cellulose plastics and esters. Intermediate molecular weight acids are used in the preparation of lubricants and lubricant additives. The higher molecular weight acids find use in the preparation of detergent products.

In U.S. Pat. No. 4,220,803, copper oxide and copper oxide-chromium oxide catalysts are disclosed as useful for the conversion of ethanol to acetic acid. Molecular oxygen was used as the oxidizing agent and selectivity to acetic acid was lower than the selectivity to acetaldehyde.

In Japanese Pat. No. 57/102835 copper oxide-zinc oxide, copper oxide-chromium oxide or copper oxide-chromium oxide-manganese oxide catalysts are disclosed as useful for converting mixtures of ethanol or acetaldehyde and water to acetic acid.

SUMMARY OF THE INVENTION

This invention provides for a process for converting alcohols to carboxylic acids with high selectivity. The process comprises contacting, in the vapor phase, alcohol, water and hydrogen, with a catalyst comprising copper, zinc, chromium and a promoter metal selected from alkali metals, alkaline earth metals, rare earth metals and mixtures thereof supported on an inert porous refractory support. The use of the instant catalyst lowers the aldehyde and ester make while increasing the acid make. The catalyst is prepared by impregnating the porous alumina support with one or more solution(s) of copper, zinc, chromium, and/or promoter salts, drying the impregnated support, calcining the support in an oxidizing atmosphere at a temperature ranging from about 100° C. to about 900° C. and then activating the calcined material in a reducing environment. A key aspect of the invention is the addition of hydrogen to the feed in order to maintain the selectivity of the catalyst for the carboxylic acid, which is surprising in view of the fact that two moles of hydrogen are produced for every mole of carboxylic acid produced. Optimum catalyst life is obtained by carrying out the reaction at pressures ranging between about 2 to about 5 atmospheres.

DESCRIPTION OF THE PREFERRED EMBODIMENTS

The alcohols to be converted by the process of the instant invention are primary alcohols, of the general formula $RCH_2OH$ where R is hydrogen, aryl of up to about $C_{30}$ or $C_1$ to about $C_{30}$ alkyl. R may be substituted with inert substituents such as chloro, fluoro, alkyl, etc. These alcohols are converted to acids of the general formula $RCO_2H$ wherein R is as defined above.

Basically, catalyst preparation comprises (1) impregnating a porous inert support with one or more solutions of the requisite salts, (2) drying and calcining at a temperature ranging from about 100° C. to about 900° C., preferably from about 200° C. to about 700° C. and most preferably from about 300° C. to about 600° C. and (3) activating the calcined material in a reducing environment.

The support or carrier employed in these catalysts in its broadest aspect is selected from the larger number of conventional, porous refractory catalyst carriers or support materials which are considered relatively inert in the presence of the feeds, products and reaction conditions of the instant process. Such conventional materials are know to persons skilled in the art and may be of natural or synthetic origin and preferably have B.E.T. surface areas greater than about 100 m$^2$/g. Very suitable supports comprise those of aluminous or siliceous composition. Examples of supports that have been used as supports for different catalysts and which could, it is believed, be used as supports for the instant catalysts are the aluminum oxides (including the materials sold under the trade name "Alundum"), charcoal, pumice, magnesia, zirconia, keiselguhr, fullers' earth, silicon carbide, porous agglomerates comprising silicon and/or silicon carbide, silica, magnesia, selected clays, artificial and natural zeolites and ceramics.

The preferred support or carrier to be utilized in preparing the catalyst comprises a porous gamma alumina having a B.E.T. surface area greater than about 100 m$^2$/g. The B.E.T. method for determining surface area is described in Brunauer, S., Emmet, P. H. and Teller, E., J. Am. Chem. Soc., 60, 309–16 (1938). Regarding purity of the alumina, it may be stated that small amounts of impurities are not generally detrimental. The most suitable aluminas for use in the present invention are found to be those having a high surface area, for instance, alumina having a surface area of at least about 100 m$^2$/g. The alumina may contain minor amounts of other compounds such as silica. Aluminas are readily available commercially which are usable in the instant invention. The following table lists several commercial aluminas and their properties which are found suitable. The Kaiser KA-201 alumina is a preferred support.

| Alumina | Surface Area, m$^2$/g | Pore Vol., cc/g | Na, ppm | $SO_4^=$, % wt | $Fe_2O_3$, % wt | Cl, % wt |
|---|---|---|---|---|---|---|
| CCI[a] | 252 | 0.8 | 160 | 0.06 | — | 0.02 |
| KA-201[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 0.51 | 0.03 | — | 0.03 |
| CATAPAL[e] | 348 | 0.91 | | | | |
| FILTROL[f] | 214 | 0.82 | | | | |

[a] Catalysts & Chemicals, Inc., now United Catalysts
[b] Kaiser
[c] Reynolds Corporation
[d] American Cyanamid Corporation
[e] Conoco Corporation
[f] Filtrol Corporation The first step in the preparation of the catalyst is to impregnate the support with solubilized salts of copper, zinc, chromium and/or promoter metal. The salts must be soluble in a suitable solubilizing media, either organic or inorganic. Water is a preferred solubilizing media. Lower alkanols also provide examples of suitable organic solvents. Suitable metal salts are, for example, chlorides, bromides, nitrates, acetates, lactates, carbonates, bicarbonates and the like. The impregnation of the support may be carried out in one step utilizing all the metal salts dissolved in a single solution, or it may be carried out in a multistep process, using one or more of the metal salts dissolved in individual impregnating solutions. A preferred impregnating process is the so-called "dry impregnation" where just a sufficient amount of impregnating solution containing all the requisite metal salts is used such that all the pore volume in the carrier is filled and no excess solution is left after impregnation. The next step is to dry and calcine the impregnated material. The drying and calcining can be carried out in individual steps. For example, drying can be carried out at temperatures up to about 150° C. followed by a calcining step at temperatures ranging from about 100° C. to about 900° C. preferably from about 300° C. to about 800° C. Preferably, the drying and calcining are carried out in one continuous step, heating the material slowly through the low temperature ranges to dry the material and then raising the temperature to the calcining conditions. The purpose of the calcining is to convert the soluble metal salts to oxides or oxygen-containing compounds upon the support material. Calcining is carried out in a neutral or oxidizing atmosphere, air being the preferred atmosphere. Nitrogen is also a suitable alternative atmosphere. The drying step is preferably carried out in the initial stages of the calcining step. Drying and calcining times are not critical and depend on temperatures. These are readily determined by simple experimentation. Five minutes to ten hours are usually sufficient, although longer times are acceptable.

In the most preferred process, a solution containing the promoter metal salts is used to impregnate the support which is then dried and calcined. The calcined material is then impregnated with a solution having copper, zinc and chromium salts dissolved therein. This material is dried, calcined and than activated prior to use.

The amount of metals deposited upon the support are not critical and may be varied through a wide range so long as they are present in sufficient amount to be catalytically effective, a condition which is readily determined by experiment. Preferably the support will contain from about 0.1 to about 20% wt of copper measured as the metal per total weight of the catalyst, from about 0.1 to about 10% wt of zinc, measured as the metal per total weight of the catalyst from about 0.01 to about 10% wt, more preferably from about 0.1 to about 5%wt of chromium, measured as the metal per total weight of the catalyst and from about 0.001 to about 10% wt, more preferably from about 0.1 to about 5% wt of promoter metal measured as the metal per total weight of the catalyst. The promoter metal is selected from alkali metals, alkaline earth metals, rare earth metals and mixtures thereof.

After calcining, the catalyst is activated in a reducing environment. The reducing environment may be either a gaseous atmosphere or a suitable liquid solution. Suitable examples of a gaseous reducing atmosphere comprise hydrogen, ammonia, carbon monoxide, and the like. The preferred atmosphere is hydrogen. Activation temperatures when utilizing a gaseous atmosphere range from about 175° C. to about 550° C. The time needed for activation in a gaseous atmosphere will depend on the temperature, the higher the temperature, the shorter the time and vice versa, and typically, useful times have been found to range from about 0.01 hour to about 24 hours, although times outside these limits are also useful, economic considerations, however, tending to dictate against their use. Reducing solutions are those typically used in the art, such as, for example, aqueous or ammoniacial solutions of hydrazine, sodium borohydride or formaldehyde or solutions of, for example, triethyl aluminum or di-isobutyl aluminum hydride in an organic solvent such as heptane. Temperatures utilized with reducing solutions range from about room temperature to about 100° C. or higher with times ranging from about 0.01 to about 10 hours or longer. Time and temperatures are not critical and will depend on the solution being utilized. They are readily determined by routine experimentation. Although not being stated as a limiting condition on the invention, it is believed that the activation of the catalyst in a reducing environment serves to at least partially reduce the copper from the +2 valence state to the +1 and/or 0 valance state, which is believed to contribute to the catalytic activity of the catalyst. Reducing conditions, however, should not be so severe as to reduce the ZnO and $Cr_2O_3$. The promoter metals, ie., the alkali metal, alkali earth metals and rare earth metals will not, even after reduction, be present on the catalyst in the form of the active free metal but will be present in oxidized form. They are believed to be present in the form of oxides or oxygen-containing compounds and may be combined with the support and/or other catalyst components. The appropriate activation conditions can readily be determined by experimentation. For example, times and temperatures can be varied and the resultant catalytic material can be examined by x-ray photoelectron spectroscopy in order to determine the activation state of the copper. Alternatively, the catalyst's catalytic activity can be determined and utilized to determine optimum activating conditions.

In practice, the alcohol to be converted is contacted along with water and hydrogen, all in the vapor phase with the catalyst of the instant invention. At least 1 mole of water per mole of alcohol is utilized. Preferably, excess water is used, say a water to alcohol mole ratio of about 3:1, preferably 5:1, and more preferably 10:1. Thus, the water to alcohol mole ratio will range from about 1:1 to about 3:1, preferably 1:1 to about 5:1 and more preferably 1:1 to about 10:1. Water to alcohol mole ratios between about 5:1 to about 10:1 are quite suitable.

Although hydrogen is generated in the reaction, the presence of an external supply of hydrogen is needed to prevent the catalyst from rapidly losing activity as a function of time. At least 1 mole of hydrogen per mole of alcohol is used. Suitable limits range between about 1:1 to about 1:10, more preferably between about 2:1 to about 8:1 moles of hydrogen per mole of alcohol.

The catalyst of this invention can be utilized in fluidized beds or packed columns, preferably the latter. The reaction is carried out at a temperature ranging from about 200° C. to about 500° C., preferably from about 250° C. to about 400° C. The reaction is carried out at relatively low pressures, say from about 0.1 to about 4 atmospheres. While the thermodynamics of the alcohol to acid reaction favors low pressures, it has been found that maximum catalyst life can be obtained when operating at pressures ranging from about 2 to about 5 atmospheres. The alcohol is fed to the reactor at liquid hourly space velocities ranging from about 1 to about 100, preferably from about 2 to about 15.

The reaction may be conducted batchwise or in a continuous operation. By way of illustration of the batchwise process, a high pressure autoclave is charged with alcohol and water and pressurized with hydrogen and heated to reaction temperature. After the reaction is allowed to proceed for the desired length of time, the autoclave is cooled, the excess hydrogen vented, and the products worked up by conventional methods. By way of illustration of continuous operation, a vertical, high-pressure column is charged with catalyst; and alcohol and water are applied at one end of the column, say the top end. At the same time hydrogen is metered into the column in cocurrent flow. During the reaction, appropriate conditions of temperature and pressure are maintained. The reaction product is removed from the bottom of the column, freed from hydrogen and worked up by conventional methods. The hydrogen is advantageously recycled to the reactor.

As used herein, the term "catalytically effective amount" of a catalyst component means an amount of a particular component that provides catalytic activity or a change in the catalytic properties of a catalyst. Examples of catalytic properties include, inter alia, operability (resistance to runaway), selectivity, activity, conversion yield and stability.

The process of this invention is further described by the following illustrative embodiments which are provided for illustration and are not to be construed as limiting the invention.

ILLUSTRATIVE EMBODIMENT

Catalyst Preparation

The following illustrates a typical preparation of a catalyst of the instant invention.

0.21 Grams of lithium hydroxide promoter were dissolved in 12 ml of water and added to 20 g of 14-30 mesh Kaiser KA-201 alumina. This material was heated in air in a muffle furnace for 1 hr each at 100, 200, and 300 degrees C. 9.5 Milliliters from a 250 ml stock solution of 0.69 m cupric nitrate, 0.40 m zinc nitrate, and 0.11 m chromium nitrate were diluted with water to 12 ml and used to impregnate the promoter treated support. The mixture was mulled during a 30 min period to allow even penetration and then transferred to a Vycor tube. A 200 ml air stream was passed over the catalyst while the temperature was raised to 500 degrees C. over a 4 hr period. Analysis of the dry catalyst showed the following weight %; Cu=6.6; Zn 4.6; Cr 0.81; Li 0.17 (as metals).

Process

The following illustrates a typical use of the above-described catalyst in the process of the instant invention.

15 Milliliters of the catalyst from the catalyst preparation example above was placed in a 1" stainless steel reactor tube that was heated with an electric furnace. Reduction of the catalyst was carried out at 1 atm, using a mixture of 200 ml/min of nitrogen and 100 ml/min hydrogen. The temperature was programmed to 100 degrees C. in 15 min, and then to 325 degrees C. in 3 hrs. The temperature was set at 310° C. for the start of the alcohol to acid reaction. The nitrogen flow was stopped, the hydrogen flow was increased to 45 psig. Nonyl alcohol and water were pumped into the reactor at 15 ml/hr each. After running for 2 hrs a sample was removed for gas chromatograph analysis. The analysis gave a 71.9% conversion of the alcohol. The weight % selectivity to products are as follows; hydrocarbon 0.17; nonanal=42.3; nonanoic acid=49.5; aldol condensates 2.09; $C_{17}$ ketone=0.68; and nonyl nonoate=5.27.

ILLUSTRATIVE EMBODIMENT I

A series of Cu-Zn-Cr of KA-201 alumina catalysts with varying amounts of Li (added as LiOH) were prepared and tested using nonyl alcohol as the feed. Samples were analyzed after 1-2 hours at reaction temperature and the results are shown in Table I.

ILLUSTRATIVE EMBODIMENT II

A series of Cu-Zn-Cr on KA-201 alumina catalysts with varying amounts of Na (added as NaOH) were prepared and tested using nonyl alcohol as the need. Samples were analyzed after 1-2 hours at reaction temperature and the results are shown in Table II.

ILLUSTRATIVE EMBODIMENT III

A series of Cu-Zn-Cr on KA-201 alumina catalysts with varying amounts of Ca (added as $Ca(NO_3)_2$) were prepared and tested using nonyl alcohol as the feed. Samples were analyzed after 1-2 hours at temperature and the results are shown in Table III.

TABLE I

| | Cat. Comp. (wt %) | | | | | Time, | Alcohol | Selectivity (wt %) | | | | | |
| --- | --- | --- | --- | --- | --- | --- | --- | --- | --- | --- | --- | --- | --- |
| Example | Cu | Zn | Cr | Li | O.C.* | Hrs. | Conv. (wt %) | Acid | Ester | Aldehyde | Hydro-carbon | Aldols | Ketone |
| I-1 | 7.0 | 4.7 | 0.87 | 0.096 | A | 2 | 67.7 | 49.8 | 10.28 | 38.4 | 1.19 | 0.61 | 0.66 |
| | | | | | B | 1 | 75.3 | 48.3 | 6.59 | 43.2 | 0.54 | 0.37 | 0.45 |
| I-2 | 6.6 | 4.6 | 1.8 | 0.1 | A | 1 | 71.0 | 52.5 | 6.01 | 39.2 | 0.10 | 1.42 | 0.70 |
| | | | | | B | 1 | 79.0 | 42.4 | 3.44 | 31.6 | 0.72 | 1.20 | 0.59 |
| I-3 | 6.6 | 4.6 | 0.81 | 0.17 | A | 2 | 71.9 | 49.5 | 5.27 | 42.3 | 0.17 | 2.09 | 0.68 |
| | | | | | B | 1.5 | 73.3 | 42.4 | 3.93 | 50.2 | 0.66 | 2.22 | 0.68 |
| I-4 | 6.6 | 4.4 | 0.8 | 0.26 | A | 2 | 60.2 | 43.1 | 9.45 | 45.2 | 0.12 | 0.78 | 0.66 |
| | | | | | B | 2 | 69.5 | 41.6 | 4.30 | 52.9 | 0.27 | 0.36 | 0.53 |
| I-5 | 6.6 | 4.4 | 0.8 | 0.58 | A | 2 | 60.3 | 54.7 | 5.69 | 37.0 | 0.38 | 0.51 | 1.01 |
| | | | | | B | 2 | 65.9 | 46.0 | 3.10 | 48.6 | 1.21 | 0.32 | 0.82 |
| I-6 | 6.9 | 4.2 | 0.79 | 0.72 | A | 2 | 59.3 | 50.6 | 3.10 | 44.9 | 0.19 | 0.47 | 0.73 |
| | | | | | B | 2 | 63.6 | 42.0 | 1.67 | 54.9 | 0.47 | 0.46 | 0.57 |

TABLE I-continued

| Example | Cat. Comp. (wt %) | | | | O.C.* | Time, Hrs. | Alcohol Conv. (wt %) | Selectivity (wt %) | | | | | |
| --- | --- | --- | --- | --- | --- | --- | --- | --- | --- | --- | --- | --- | --- |
| | Cu | Zn | Cr | Li | | | | Acid | Ester | Aldehyde | Hydro-carbon | Aldols | Ketone |
| I-7 | 6.6 | 4.4 | 0.8 | 0.87 | A | 2 | 61.0 | 56.4 | 3.59 | 36.9 | 1.56 | 0.61 | 1.07 |

O.C. — Operating Conditions:
A 15 ml/hr alcohol
15 ml/hr $H_2O$
125 ml/min Hydrogen
Temp. - 310° C.
Press - 45 psig
B 30 ml/hr alcohol
30 ml/hr $H_2O$
250 ml/min Hydrogen
Temp. - 330° C.
Press - 45 psig

TABLE II

| Example | Cat. Comp. (wt %) | | | | Time, Hrs. | O.C.* | Alcohol Conv. (wt %) | Selectivity (wt %) | | | | | |
| --- | --- | --- | --- | --- | --- | --- | --- | --- | --- | --- | --- | --- | --- |
| | Cu | Zn | Cr | Na | | | | Acid | Ester | Aldehyde | Hydro-carbon | Aldols | Ketone |
| II-1 | 6.6 | 4.4 | 0.8 | 0.52 | 2 | A | 66.5 | 52.2 | 3.7 | 42.4 | 0.12 | 0.42 | 0.77 |
| | | | | | 2 | B | 72.6 | 46.6 | 1.82 | 50.0 | 0.21 | 0.33 | 0.63 |
| II-2 | 6.6 | 4.4 | 0.8 | 0.71 | 2 | A | 64.5 | 56.6 | 5.95 | 35.0 | 1.04 | 0.38 | 0.98 |
| | | | | | 1.5 | B | 70.8 | 48.4 | 3.01 | 45.8 | 1.86 | 0.20 | 0.81 |
| II-3 | 6.6 | 4.4 | 0.8 | 2.9 | 2 | A | 60.1 | 43.8 | 7.32 | 44.8 | 0.28 | 1.56 | 2.41 |
| | | | | | 1.5 | B | 65.5 | 37.3 | 2.79 | 56.0 | 0.61 | 1.01 | 2.26 |

O.C. — Operating Conditions:
A 15 ml/hr alcohol
15 ml/hr $H_2O$
125 ml/min Hydrogen
Temp. - 310° C.
Press - 45 psig
B 30 ml/hr alcohol
30 ml/hr $H_2O$
250 ml/min Hydrogen
Temp. - 330° C.
Press - 45 psig

TABLE III

| Example | Cat. Comp. (wt %) | | | | Time Hrs. | O.C.* | Alcohol Conv. (wt %) | Selectivity (wt %) | | | | | |
| --- | --- | --- | --- | --- | --- | --- | --- | --- | --- | --- | --- | --- | --- |
| | Cu | Zn | Cr | Ca | | | | Acid | Ester | Aldehyde | Hydro-carbon | Aldols | Ketone |
| III-1 | 6.9 | 4.7 | 0.85 | 0.27 | 2 | A | 60.5 | 46.3 | 4.73 | 47.6 | 0.13 | 0.40 | 0.83 |
| | | | | | 2 | B | 76.8 | 49.7 | 2.58 | 45.8 | 0.82 | 0.26 | 0.83 |
| III-2 | 7.0 | 4.3 | 0.84 | 1.7 | 2 | A | 59.3 | 51.4 | 4.65 | 42.0 | 0.19 | 0.93 | 0.79 |
| | | | | | 2 | B | 64.8 | 43.8 | 1.91 | 52.6 | 0.63 | 0.41 | 0.66 |
| III-3 | 6.6 | 4.4 | 0.8 | 1.5 | 2 | A | 63.9 | 54.9 | 8.20 | 31.9 | 0.85 | 2.83 | 1.30 |
| | | | | | 1.5 | B | 68.9 | 48.6 | 4.04 | 41.5 | 2.22 | 2.28 | 1.29 |

*O.C. — Operating Conditions:
A 15 ml/hr alcohol
15 ml/hr $H_2O$
125 ml/min Hydrogen
Temp. - 310° C.
Press - 45 psig
B 30 ml/hr alcohol
30 ml/hr $H_2O$
250 ml/min Hydrogen
Temp. - 330° C.
Press - 45 psig

ILLUSTRATIVE EMBODIMENT IV

A series of Cu-Zn-Cr on KA-201 alumina catalysts with different promoters were prepared and tested using nonyl alcohol as the feed. Samples were analyzed after 1-2 hours at temperature and the results are shown in Table IV.

TABLE IV

| Example | Cat. Comp. (wt %) | | | | O.C.* | Time, Hrs. | Alcohol Conv. (wt %) | Selectivity (wt %) | | | | | |
| --- | --- | --- | --- | --- | --- | --- | --- | --- | --- | --- | --- | --- | --- |
| | Cu | Zn | Cr | Promoter | | | | Acid | Ester | Aldehyde | Hydro-carbon | Aldols | Ketone |
| IV-1 | 6.6 | 4.4 | 0.8 | Ba/1.7 | A | 2 | 55.7 | 41.5 | 11.4 | 45.1 | 0.57 | 1.24 | 0.68 |
| | | | | | B | 1.5 | 58.6 | 34.5 | 7.20 | 56.0 | 0.58 | 1.18 | 0.67 |
| IV-2 | 6.6 | 4.4 | 0.8 | Ba/1.7 | A | 2 | 63.5 | 53.7 | 12.7 | 29.6 | 1.53 | 1.21 | 1.21 |
| | | | | | B | 1.5 | 71.3 | 51.8 | 7.78 | 35.6 | 2.73 | 0.98 | 1.16 |
| IV-3 | 6.6 | 4.4 | 0.8 | Mg/1.3 | A | 2 | 58.1 | 53.9 | 5.87 | 36.1 | 1.08 | 2.39 | 0.65 |
| | | | | | B | 2 | 67.8 | 51.8 | 5.35 | 38.3 | 2.39 | 1.27 | 0.84 |
| IV-4 | 6.6 | 4.4 | 0.8 | La/1.5 | A | 2 | 63.3 | 52.8 | 13.3 | 30.0 | 1.03 | 0.93 | 1.85 |

TABLE IV-continued

| Example | Cat. Comp. (wt %) | | | | O.C.* | Time, Hrs. | Alcohol Conv. (wt %) | Selectivity (wt %) | | | | | |
| | Cu | Zn | Cr | Promoter | | | | Acid | Ester | Aldehyde | Hydro-carbon | Aldols | Ketone |
|---|---|---|---|---|---|---|---|---|---|---|---|---|---|
| | | | | | B | 1.5 | 70.3 | 51.5 | 6.98 | 38.3 | 1.10 | 0.74 | 1.49 |

*O.C. — Operating Conditions:
A 15 ml/hr alcohol
15 ml/hr H$_2$O
125 ml/min Hydrogen
Temp. - 310° C.
Press - 45 psig
B 30 ml/hr alcohol
30 ml/hr H$_2$O
250 ml/min Hydrogen
Temp. - 330° C.
Press - 45 psig

ILLUSTRATIVE EMBODIMENT V

Comparative life tests were made on two Cu-Zn-Cr-Na/Ra-1 alumina catalysts. The feed in both cases consisted of 15 ml/hr of nonyl alcohol and 15 ml/hr of H$_2$O. For Example V-1, hydrogen (125 ml/min) was fed continuously throughout the run. For Example IV-2 hydrogen (125 ml/min) was fed only during the first two hours and then cut off. The ratio of carboxylic acid to aldehyde produced was determined and reported to Table V. As can be seen from the results, hydrogen must be added to the test to maintain the long term activity of the catalyst, although there may be a short term increase in acid production due to a more favorable thermodynamic equilibrium situation.

TABLE V

| Catalyst V-1 | | | Catalyst V-2 | | |
|---|---|---|---|---|---|
| Rx Temp, °C. | Hrs at Temp. | RCO$_2$H/RCHO | Rx Temp, °C. | Hrs at Temp. | RCO$_2$H/RCHO |
| 300 | 2 | 1.68 | 310 | 2 | 1.39 |
| 310 | 2 | 1.69 | 310 | 1.5 | 2.09 |
| 310 | 21 | 1.56 | 310 | 18 | 1.20 |
| 310 | 48 | 1.71 | 310 | 25 | 0.65 |
| | | | 310 | 47 | 0.57 |

ILLUSTRATIVE EMBODIMENT VI

A catalyst was prepared in a manner similar to that described above using as a support Davison Grade 57 SiO$_2$ (Surface area—300 m$^2$/g; pore vol.—1.0 cc/g; density—0.4 g/cc). The catalyst was tested using nonyl alcohol as feed. Samples were analyzed after 1–2 hours at temperature and the results are shown in Table VI.

TABLE VI

| Example | Cat. Comp. (wt %) | | | | O.C.* | Time, Hrs. | Alcohol Conv. (wt %) | Selectivity (wt %) | | | | | |
| | Cu | Zn | Cr | Na | | | | Acid | Ester | Aldehyde | Hydro-carbon | Aldols | Ketone |
|---|---|---|---|---|---|---|---|---|---|---|---|---|---|
| VI-1 | 6.4 | 4.2 | 0.76 | 0.38 | A | 2 | 64.8 | 27.8 | 20.1 | 50.5 | 0.29 | 1.31 | Trace |
| | | | | | B | 1.5 | 65.5 | 22.9 | 11.3 | 63.8 | 0.31 | 1.51 | 0.21 |

*O.C. — Operating Conditions:
A 15 ml/hr alcohol
15 ml/hr H$_2$O
125 ml/min Hydrogen
Temp. - 310° C.
Press - 45 psig
B 30 ml/hr alcohol
30 ml/hr H$_2$O
250 ml/min Hydrogen
Temp. - 330° C.
Press - 45 psig

I claim:

1. A process for converting alcohols to carboxylic acids which process comprises contacting in the vapor phase said alcohols, water and added hydrogen at a temperature ranging from about 200° C. to about 500° C. with a catalyst comprising catalytically effective amounts of copper, zinc, chromium and a promoter selected from the group consisting of alkali metals, alkaline earth metals, rare earth metals and mixtures thereof supported on a porous refractory support.

2. The process of claim 1 wherein the refractory support is alumina.

3. The process of claim 2 wherein the alumina has a surface area greater than about 100 m$^2$/g.

4. The process of claim 1 wherein the temperature ranges from about 250° C. to about 400° C.

5. The process of claim 1 wherein the pressure ranges from about 0.1 to about 10 atmosphere.

6. The process of claim 4 wherein the pressure ranges from about 1 to about 5 atmospheres.

7. The process of any of claims 1–6 wherein at least one mole of hydrogen is added for each mole of alcohol present.

8. The process of any of claims 1–6 wherein the copper, measured as the metal, ranges from about 0.1 to about 20 percent by weight of the total catalyst, the zinc, measured as the metal, ranges from about 0.1 to about 10 percent by weight of the total catalyst, the chromium, measured as the metal, ranges from about 0.01 to about 10 percent by weight of the total catalyst and the promoter, measured as the metal, ranges from about 0.001 to about 10 percent by weight of the total catalyst.

9. The process of claim 8 wherein at least one mole of hydrogen is added for each mole of alcohol present.

10. A process for converting alcohols to carboxylic acids which process comprises contacting in the vapor phase said alcohols, water and added hydrogen at a temperature ranging from about 250° C. to about 400° C. with a catalyst comprising copper, zinc, chromium and a promoter selected from the group consisting of alkali metals, alkaline earth metals, rare earth metals and mixtures thereof supported on a porous alumina support having a surface area greater than about 100 m$^2$/g wherein the copper, measured as the metal, ranges from about 0.1 to about 20 percent by weight of the total catalyst, the zinc, measured as the metal, ranges from about 0.1 to about 10 percent by weight of the total catalyst the chromium, measured as the metal, ranges from about 0.1 to about 5 percent by weight of the total catalyst and the promoter, measured as the metal, ranges from about 0.1 to about 5 percent by weight of the total catalyst.

11. The process of claim 10 wherein the promoter is selected from sodium, potassium, lithium, calcium, magnesium, lanthanum and mixtures thereof.

12. The process of claims 10 or 11 wherein at least one mole of hydrogen is added for each mole of alcohol present.

* * * * *